(12) United States Patent
Hardert (10) Patent No.: US 7,708,753 B2
(45) Date of Patent: May 4, 2010

(54) BALLOON CATHETER WITH EXTENDABLE DILATION WIRE

(75) Inventor: Michael W Hardert, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 778 days.

(21) Appl. No.: 11/525,371

(22) Filed: Sep. 21, 2006

(65) Prior Publication Data

US 2007/0073329 A1 Mar. 29, 2007

Related U.S. Application Data

(60) Provisional application No. 60/721,017, filed on Sep. 27, 2005.

(51) Int. Cl.
*A61M 29/00* (2006.01)
(52) U.S. Cl. .................................... 606/192; 606/128
(58) Field of Classification Search .................. 604/8, 604/96, 104, 105, 280, 281; 606/8, 159, 606/191–194, 198, 127, 128; 623/1, 12, 623/13
See application file for complete search history.

(56) References Cited

U.S. PATENT DOCUMENTS

| 4,535,757 | A | 8/1985 | Webster, Jr. ............. 128/1 D |
| 4,729,763 | A | 3/1988 | Henrie ..................... 604/22 |
| 4,877,030 | A | 10/1989 | Beck et al. ................ 128/343 |
| 4,886,061 | A | 12/1989 | Fischell et al. ........... 128/305 |
| 4,898,575 | A | 2/1990 | Fischell et al. ............ 604/22 |
| 4,983,167 | A | 1/1991 | Sahota .................... 606/194 |
| 5,019,042 | A | 5/1991 | Sahota .................... 604/101 |
| 5,030,201 | A | 7/1991 | Palestrant ................. 604/22 |
| 5,047,040 | A | 9/1991 | Simpson et al. ........... 606/159 |
| 5,057,120 | A | 10/1991 | Farcot .................... 606/194 |
| 5,078,723 | A | 1/1992 | Dance et al. .............. 606/159 |
| 5,080,660 | A | 1/1992 | Buelna .................... 606/45 |
| 5,090,958 | A | 2/1992 | Sahota .................... 604/98 |
| 5,147,377 | A | 9/1992 | Sahota .................... 606/194 |
| 5,160,321 | A | 11/1992 | Sahota .................... 604/96 |
| 5,181,920 | A | 1/1993 | Mueller et al. ............ 606/159 |
| 5,192,291 | A | 3/1993 | Pannek, Jr. ............... 606/159 |
| 5,196,024 | A | 3/1993 | Barath .................... 606/159 |
| 5,209,749 | A | * | 5/1993 | Buelna .................... 606/45 |
| 5,224,945 | A | 7/1993 | Pannek, Jr. ............... 606/159 |
| 5,224,949 | A | 7/1993 | Gomringer et al. ......... 606/159 |
| 5,320,605 | A | 6/1994 | Sahota .................... 604/101 |

(Continued)

FOREIGN PATENT DOCUMENTS

EP 0 117 519 9/1984

(Continued)

*Primary Examiner*—Julian W Woo
*Assistant Examiner*—Richard Dault
(74) *Attorney, Agent, or Firm*—Brinks Hofer Gilson & Lione (57) ABSTRACT

A balloon catheter is provided which may be used to dilate hardened regions of stenosis. The balloon catheter is provided with dilation wires that may be extended so that the dilation wires are disposed adjacent an outer surface of the balloon during dilation. Thus, as the balloon is expanded, the dilation wires are squeezed between the balloon and the stenosed region to crack or breakup the stenosis. The dilation wires may also be retracted away from the balloon. Thus, the stenosed region may be dilated with the balloon without using the dilation wires if desired.

13 Claims, 4 Drawing Sheets

U.S. PATENT DOCUMENTS

| | | | |
|---|---|---|---|
| 5,320,634 A | 6/1994 | Vigil et al. | 606/159 |
| 5,336,178 A | 8/1994 | Kaplan et al. | 604/53 |
| 5,372,601 A | 12/1994 | Lary | 606/159 |
| 5,395,332 A | 3/1995 | Ressemann et al. | 604/96 |
| 5,409,454 A | 4/1995 | Fischell et al. | 604/22 |
| 5,411,478 A | 5/1995 | Stillabower | 604/96 |
| 5,431,673 A | 7/1995 | Summers et al. | 606/170 |
| 5,441,510 A | 8/1995 | Simpson et al. | 606/159 |
| 5,450,843 A | 9/1995 | Moll et al. | 600/207 |
| 5,505,725 A | 4/1996 | Samson | 606/7 |
| 5,522,790 A | 6/1996 | Moll et al. | 600/204 |
| 5,556,408 A | 9/1996 | Farhat | 606/180 |
| 5,569,277 A | 10/1996 | Evans et al. | 606/159 |
| 5,571,087 A | 11/1996 | Ressemann et al. | 604/96 |
| 5,575,771 A | 11/1996 | Walinsky | 604/96 |
| 5,609,628 A | 3/1997 | Keranen | 623/1 |
| 5,616,149 A | 4/1997 | Barath | 606/159 |
| 5,628,746 A | 5/1997 | Clayman | 606/45 |
| 5,722,979 A | 3/1998 | Kusleika | 606/108 |
| 5,728,129 A | 3/1998 | Summers | 606/170 |
| 5,779,698 A | 7/1998 | Clayman et al. | 606/39 |
| 5,792,158 A | 8/1998 | Lary | 606/159 |
| 5,797,935 A * | 8/1998 | Barath | 606/159 |
| 5,904,679 A | 5/1999 | Clayman | 606/39 |
| 5,910,144 A | 6/1999 | Hayashi | 606/108 |
| 5,921,958 A | 7/1999 | Ressemann et al. | 604/96 |
| 5,941,869 A | 8/1999 | Patterson et al. | 604/508 |
| 6,036,689 A | 3/2000 | Tu et al. | 604/41 |
| 6,036,708 A | 3/2000 | Sciver | 606/159 |
| 6,071,285 A | 6/2000 | Lashinski et al. | 606/108 |
| 6,123,718 A | 9/2000 | Tu et al. | 607/113 |
| 6,165,187 A | 12/2000 | Reger | 606/159 |
| 6,231,572 B1 | 5/2001 | Hart et al. | 606/45 |
| 6,245,040 B1 | 6/2001 | Inerbitzen et al. | 604/103.07 |
| 6,254,608 B1 | 7/2001 | Solar | 606/108 |
| 6,280,464 B1 | 8/2001 | Hayashi | 623/1.11 |
| 6,283,947 B1 | 9/2001 | Mirzaee | 604/264 |
| 6,306,151 B1 | 10/2001 | Lary | 606/159 |
| 6,355,013 B1 | 3/2002 | van Muiden | 604/96.01 |
| 6,500,186 B2 | 12/2002 | Lafontaine et al. | 606/159 |
| 6,508,824 B1 | 1/2003 | Flaherty et al. | 606/185 |
| 6,629,953 B1 | 10/2003 | Boyd | 604/106 |
| 6,632,231 B2 | 10/2003 | Radisch, Jr. | 606/159 |
| 6,746,463 B1 | 6/2004 | Schwartz | 606/159 |
| 6,808,531 B2 | 10/2004 | Lafontaine et al. | 606/159 |
| 6,885,124 B2 | 4/2005 | Neet | 310/208 |
| 6,966,889 B2 | 11/2005 | Saab | 604/96.01 |
| 7,396,358 B2 * | 7/2008 | Appling et al. | 606/159 |
| 7,566,319 B2 * | 7/2009 | McAuley et al. | 604/103.08 |
| 2001/0051810 A1 | 12/2001 | Dubrul et al. | 606/159 |
| 2003/0028212 A1 | 2/2003 | Saab | 606/192 |
| 2003/0040754 A1 | 2/2003 | Mitchell et al. | 606/106 |
| 2003/0114868 A1 | 6/2003 | Fischell et al. | 606/159 |
| 2003/0114877 A1 | 6/2003 | Gellman | 606/192 |
| 2003/0144677 A1 | 7/2003 | Lary | 606/159 |
| 2003/0153870 A1 | 8/2003 | Meyer et al. | 604/96.01 |
| 2003/0229370 A1 | 12/2003 | Miller | 606/159 |
| 2004/0006306 A1 * | 1/2004 | Evans et al. | 604/101.03 |
| 2004/0111108 A1 | 6/2004 | Farnan | 606/194 |
| 2004/0122457 A1 | 6/2004 | Weber | 606/159 |
| 2004/0122465 A1 | 6/2004 | McMurtry et al. | 606/194 |
| 2004/0127920 A1 | 7/2004 | Radisch, Jr. | 606/159 |
| 2004/0143287 A1 | 7/2004 | Konstantino et al. | 606/194 |
| 2004/0193196 A1 | 9/2004 | Appling et al. | 606/167 |
| 2004/0199191 A1 | 10/2004 | Schwartz | 606/159 |
| 2004/0230178 A1 | 11/2004 | Wu | 604/527 |
| 2004/0243158 A1 | 12/2004 | Konstantino et al. | 606/159 |
| 2005/0021070 A1 | 1/2005 | Feld et al. | 606/194 |
| 2005/0021071 A1 | 1/2005 | Konstantino et al. | 606/194 |
| 2005/0033334 A1 | 2/2005 | Santra et al. | 606/159 |
| 2005/0090845 A1 | 4/2005 | Boyd | 606/159 |
| 2005/0090846 A1 | 4/2005 | Pedersen et al. | 606/159 |
| 2006/0085026 A1 * | 4/2006 | Appling et al. | 606/194 |
| 2006/0149308 A1 | 7/2006 | Melsheimer et al. | 606/192 |
| 2006/0173487 A1 | 8/2006 | Uflacker et al. | 606/198 |

FOREIGN PATENT DOCUMENTS

| | | |
|---|---|---|
| WO | 2004/060460 | 7/2004 |
| WO | WO 2004/066852 A3 | 8/2004 |

* cited by examiner

BALLOON CATHETER WITH EXTENDABLE DILATION WIRE

This application claims priority to U.S. Provisional Application No. 60/721,017, filed Sep. 27, 2005, which is hereby incorporated by reference herein.

BACKGROUND

The present invention relates generally to medical devices and more particularly to balloon catheters used to dilate narrowed portions of a lumen.

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, coronary angioplasty using a balloon catheter has drawn particular attention from the medical community because of the growing number of people suffering from heart problems associated with stenosis. This has lead to an increased demand for medical procedures to treat such problems. The widespread frequency of heart problems may be due to a number of societal changes, including the tendency of people to exercise less while eating greater quantities of unhealthy foods, in conjunction with the fact that people generally now have longer life spans than previous generations. Angioplasty procedures have become a popular alternative for treating coronary stenosis because angioplasty procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for coronary artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the coronary artery to be treated. During this stage, the balloon is uninflated and collapsed onto the shaft of the catheter in order to present a low profile which may be passed through the arterial lumens. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the arteries. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure. Although the treatment of stenosed coronary arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters. Although the inventions described below may be useful in treating hardened regions of stenosis, the claimed inventions may also solve other problems as well.

SUMMARY

A balloon catheter is described with dilation wires that may be used to dilate hardened regions of stenosis. The wires may be retracted away from the balloon and extended so that the dilation wires are adjacent an outer surface of the balloon. When the balloon is inflated, the dilation wires are squeezed between the balloon and the stenosed region. As a result, the dilation wires may crack and/or breakup the stenosed region. The stenosed region may also be dilated without using the dilation wires by retracting the dilation wires away from the balloon. Additional details and advantages are described below in the detailed description.

The invention may include any of the following aspects in various combinations and may also include any other aspect described below in the written description or in the attached drawings.

A balloon catheter for dilation of a lumen, comprising:

a shaft extending between a proximal portion and a distal portion, the distal portion adapted to be introduced into a body lumen, and the proximal portion adapted to remain outside of the body lumen to manipulate the distal portion;

a balloon mounted on the distal portion of the shaft, the shaft having an inflation lumen extending therethrough in fluid communication with an interior region of the balloon, the balloon thereby being expandable between a deflated state and an inflated state, wherein at least a length of an outer surface of the balloon comprises a working diameter adapted to dilate the body lumen, the length extending between a balloon proximal end and a balloon distal end; and at least two dilation wires extending along the distal portion of the shaft to the proximal portion of the shaft, wherein each of the dilation wires is positionable between a retracted position and an extended position, a distal end of each of the dilation wires being disposed proximal from the balloon proximal end in the retracted position, and the distal end of each of the dilation wires being disposed distal from the balloon proximal end in the extended position, the dilation wires thereby being disposed adjacent at least a portion of the working diameter of the balloon in the extended positions.

The balloon catheter further comprising a moveable member connected to a proximal end of each of the dilation wires, whereby movement of the moveable member causes the dilation wires to move together between the retracted position and the extended position.

The balloon catheter further comprising a proximal stop and a distal stop, the moveable member being disposed between the proximal stop and the distal stop, wherein the moveable member abuts the proximal stop when the dilation wires are in the retracted position and the moveable member abuts the distal stop when the dilation wires are in the extended position.

The balloon catheter further comprising at least two dilation wire lumens extending longitudinally through the shaft, one of the dilation wires being disposed within each of the dilation wire lumens, wherein each of the dilation wire lumens has a distal opening and the dilation wires are extendable and retractable through the distal openings, a wire length of each of the dilation wires thereby being disposed within each of the dilation wire lumens in the retracted position and the wire length being disposed adjacent the working diameter of the balloon in the extended position.

The balloon catheter wherein the dilation wires are made of superelastic alloy, each of the dilation wires being formed to have a non-linear shape in a relaxed state, whereby the non-linear shapes are straightened by the dilation wire lumens in the retracted position and the non-linear shapes are released in the extended position, the non-linear shapes of the dilation wires thereby being disposed adjacent the working diameter of the balloon in the extended positions.

The balloon catheter further comprising an annular connector attached to the distal ends of the dilation wires.

The balloon catheter further comprising an annular connector attached to the distal ends of the dilation wires.

The balloon catheter further comprising at least two dilation wire lumens extending longitudinally through the shaft, each of the dilation wire lumens having a distal opening, one of the dilation wires being disposed within each of the dilation wire lumens, the dilation wires being extendable and retractable through the distal openings, wherein a wire length of each of the dilation wires is disposed within each of the dilation wire lumens in the retracted position and the wire length is disposed adjacent the working diameter of the balloon in the extended position, and further comprising a moveable member disposed along the proximal portion of the shaft, the moveable member being connected to a proximal end of each of the dilation wires, whereby movement of the moveable member causes the dilation wires to move together between the retracted position and the extended position.

The balloon catheter further comprising a proximal stop and a distal stop, the moveable member being disposed between the proximal stop and the distal stop, wherein the moveable member abuts the proximal stop when the dilation wires are in the retracted position and the moveable member abuts the distal stop when the dilation wires are in the extended position, and wherein the dilation wires are made of superelastic alloy, each of the dilation wires being formed to have a non-linear shape in a relaxed state, whereby the non-linear shapes are straightened by the dilation wire lumens in the retracted position and the non-linear shapes are released in the extended position, the non-linear shapes of the dilation wires thereby being disposed adjacent the working diameter of the balloon in the extended positions.

A balloon catheter for dilation of a lumen, comprising:
a shaft extending between a proximal portion and a distal portion, the distal portion adapted to be introduced into a body lumen, and the proximal portion adapted to remain outside of the body lumen to manipulate the distal portion;
a balloon mounted on the distal portion of the shaft, the shaft having an inflation lumen extending therethrough in fluid communication with an interior region of the balloon, the balloon thereby being expandable between a deflated state and an inflated state, wherein at least a length of an outer surface of the balloon comprises a working diameter adapted to dilate the body lumen, the length extending between a balloon proximal end and a balloon distal end; and
at least two dilation wires extending along at least the distal portion of the shaft, each of the dilation wires comprising a distal end, the distal ends characterized by not being connected to each other, wherein each of the dilation wires is positionable between a retracted position and an extended position, the distal end of each of the dilation wires being disposed proximal from the balloon proximal end in the retracted position, and the distal end of each of the dilation wires being disposed distal from the balloon proximal end in the extended position, the dilation wires thereby being disposed adjacent at least a portion of the working diameter of the balloon in the extended positions.

The balloon catheter further comprising a moveable member connected to a proximal end of each of the dilation wires, whereby movement of the moveable member causes the dilation wires to move together between the retracted position and the extended position.

The balloon catheter further comprising a proximal stop and a distal stop, the moveable member being disposed between the proximal stop and the distal stop, wherein the moveable member abuts the proximal stop when the dilation wires are in the retracted position and the moveable member abuts the distal stop when the dilation wires are in the extended position.

The balloon catheter further comprising at least two dilation wire lumens extending longitudinally through the shaft, one of the dilation wires being disposed within each of the dilation wire lumens, wherein each of the dilation wire lumens has a distal opening and the dilation wires are extendable and retractable through the distal openings, a wire length of each of the dilation wires thereby being disposed within each of the dilation wire lumens in the retracted position and the wire length being disposed adjacent the working diameter of the balloon in the extended position.

The balloon catheter wherein the dilation wires are made of superelastic alloy, each of the dilation wires being formed to have a non-linear shape in a relaxed state, whereby the non-linear shapes are straightened by the dilation wire lumens in the retracted position and the non-linear shapes are released in the extended position, the non-linear shapes of the dilation wires thereby being disposed adjacent the working diameter of the balloon in the extended positions.

The balloon catheter further comprising a moveable member disposed along the proximal portion of the shaft, the moveable member being connected to a proximal end of each of the dilation wires, whereby movement of the moveable member causes the dilation wires to move together between the retracted position and the extended position, and further comprising a proximal stop and a distal stop, the moveable member being disposed between the proximal stop and the distal stop, wherein the moveable member abuts the proximal stop when the dilation wires are in the retracted position and the moveable member abuts the distal stop when the dilation wires are in the extended position.

A method of dilating a lumen, comprising:
introducing a balloon and a dilation wire into a body lumen, wherein a distal end of the dilation wire is disposed proximal from the balloon during the introducing;
extending the dilation wire until a stop is contacted, the stop being disposed so that at least a portion of the dilation wire is disposed adjacent a working diameter of the balloon when the stop is contacted;

inflating the balloon to dilate the body lumen, the dilation wire being disposed between the working diameter of the balloon and the body lumen during the inflating;

deflating the balloon; and withdrawing the balloon and the dilation wire from the body lumen.

The method wherein the extending comprises pulling the balloon in a proximal direction without substantially moving the dilation wire relative to the body lumen.

A method of dilating a lumen, comprising:

introducing a balloon and a dilation wire into a body lumen;

inflating the balloon to a first inflation to dilate the body lumen, the dilation wire being disposed between at least a portion of a working diameter of the balloon and the body lumen;

deflating the balloon after the first inflation;

retracting the dilation wire until a stop is contacted, the stop being disposed so that a distal end of the dilation wire is disposed proximal from the working diameter of the balloon when the stop is contacted, the retracting being performed without substantially moving the balloon;

inflating the balloon to a second inflation to dilate the body lumen without the dilation wire being disposed between the working diameter of the balloon and the body lumen; and deflating the balloon after the second inflation; and withdrawing the balloon and the dilation wire from the body lumen.

The method wherein the distal end of the dilation wire is disposed proximal from the working diameter of the balloon during the introducing, and further comprising extending the dilation wire before the first inflation until another stop is contacted, the another stop being disposed so that the distal end of the dilation wire is disposed adjacent at least a portion of the working diameter of the balloon when the another stop is contacted.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
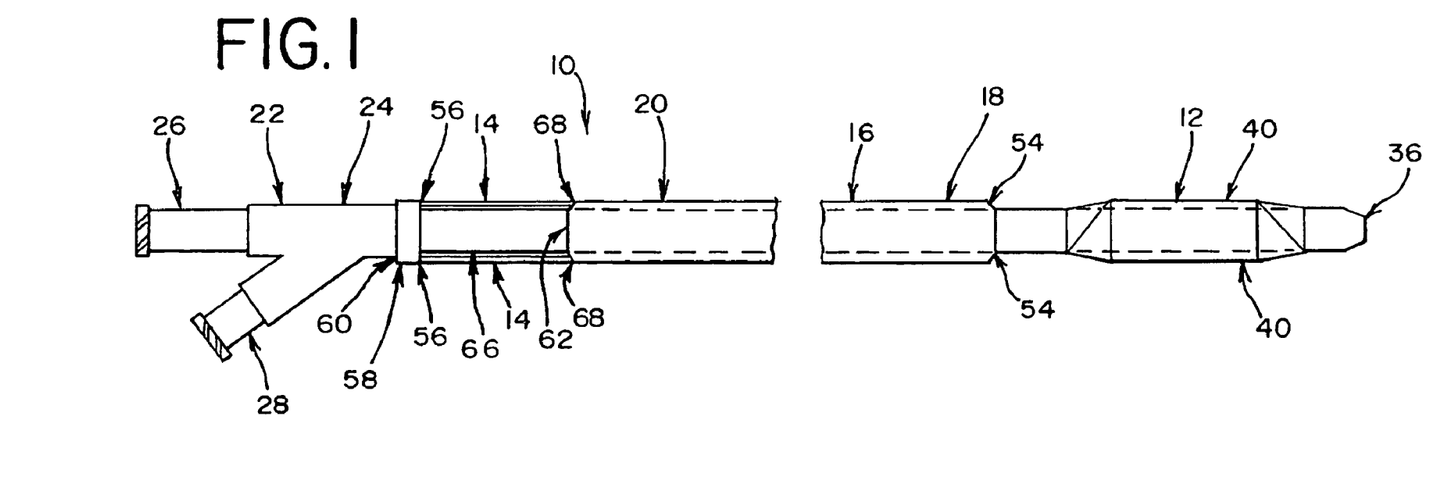
FIG. 1 is a side elevational view of a balloon catheter, showing the balloon deflated and dilation wires retracted.
Figure 2:
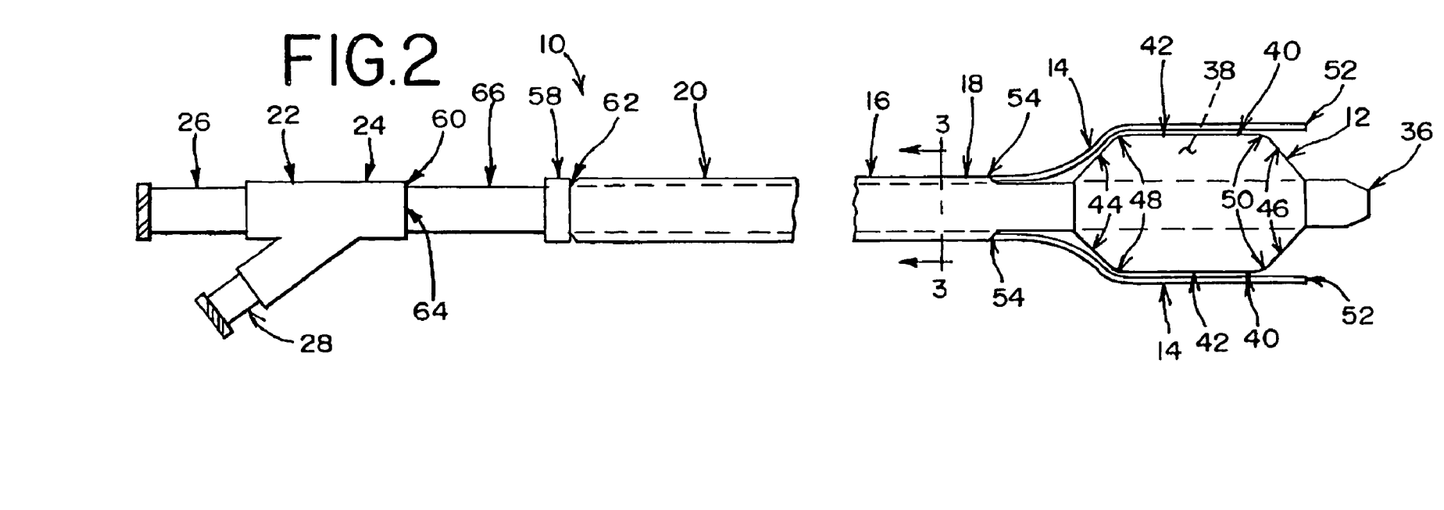
FIG. 2 is a side elevational view of the balloon catheter, showing the balloon inflated and the dilation wires extended.
Figure 3:
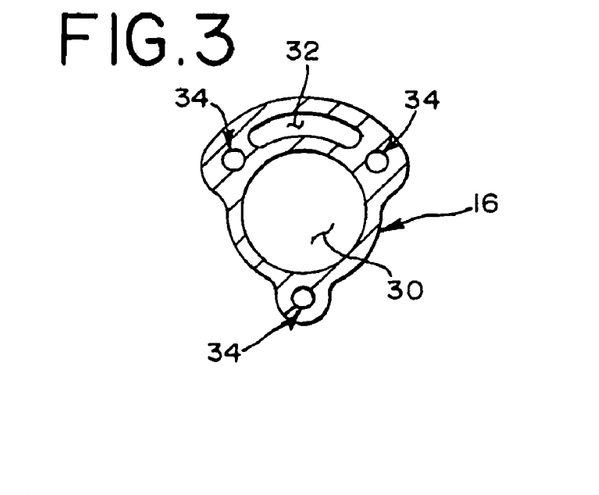
FIG. 3 is a cross-sectional view of the balloon catheter along line 3-3 of FIG. 2.

Referring now to the drawings, and particularly to FIGS. 1 through 3, a balloon catheter 10 is shown. In FIG. 1, the balloon catheter 10 is shown with the balloon 12 deflated and the dilation wires 14 retracted. In FIG. 2, the balloon catheter 10 is shown with the balloon 12 inflated and the dilation wires 14 extended. The manner of operation of the balloon catheter 16 and one preferred procedure for using the balloon catheter 10 is described in further detail below.

The balloon catheter 10 includes a shaft 16 with a distal portion 18 and a proximal portion 20. The distal portion 18 of the shaft 16 is designed to be introduced into a lumen of a patient, such as an artery. The proximal portion 20 of the shaft 16 is designed to remain outside of the patient's body so that the distal portion 18 of the shaft 16 may be manipulated inside a body lumen by a physician handling the proximal portion 20. A manifold 22 may be provided at the proximal end 24 of the shaft 16. Typically, the manifold 22 may have a guidewire port 26 designed to receive a guidewire and an inflation port 28 designed to receive an inflation medium.

As shown in FIG. 3, the shaft 16 may have a guidewire lumen 30, an inflation lumen 32, and multiple dilation wire lumens 34. The guidewire lumen 30 is in communication with the guidewire port 26. Typically, the guidewire lumen 30 extends longitudinally through the shaft 16 to the distal end 36 of the shaft 16. Thus, the guidewire lumen 30 may be used to thread the balloon catheter 10 through narrow, tortuous vessels in a manner well known to those in the art. The inflation lumen 32 is in fluid communication with the interior region 38 of the balloon 12. Thus, the balloon 12 may be inflated by supplying a pressurized fluid, such as saline, to the inflation port 28. Similarly, the balloon 12 may be deflated from the inflated state by applying a negative pressure to the inflation port, which draws the fluid out of the balloon 12. As described further below, the shaft 16 may also have one or more dilation wire lumens 34 spaced equally about the guidewire lumen 30.

As shown in FIG. 2, the outer surface 40 of the balloon has a working diameter 42 that extends along part of the length of the balloon 12. Typically, the working diameter 42 of the balloon 12 is a portion that inflates to a generally uniform circumference in order to evenly dilate a section of a lumen. However, the working diameter 42 does not necessarily to have to have a uniform circumference. The working diameter 42 of the balloon 12 may be connected to the shaft 16 with a tapered proximal portion 44 and a tapered distal portion 46. The length of the working diameter 42 may be defined as the distance between the balloon proximal end 48, where the tapered proximal portion 44 meets the working diameter 42, and the balloon distal end 50, where the tapered distal portion 46 meets the working diameter 42.

The balloon catheter 10 may also be provided with one or more dilation wires 14. The dilation wires 14 may be made from metallic, plastic or other materials. As shown in FIG. 2, the dilation wires 14 may be extended so that a portion of the dilation wires 14 are adjacent the working diameter 42 of the balloon 12. As shown in FIG. 1, the dilation wires 14 may also be retracted away from the balloon 12 so that the distal ends 52 of the dilation wires 14 (shown in FIG. 2) are proximal from at least the proximal end 48 of the balloon 12. Preferably, as shown in FIG. 2, the distal ends 52 of the dilation wires 14 are distal from the distal end 50 of the balloon 12 in the extended position. In addition as shown in FIG. 1, the distal ends 52 of the dilation wires 14 are preferably positioned within the dilation wire lumens 34 in the retracted position.

The dilation wires 14 may extend through the dilation wire lumens 34 between the proximal portion 20 of the shaft 16 and the distal portion 18 of the shaft 16. Thus, the dilation wires 14 are extendable and retractable through the distal openings 54 of the dilation wire lumens 34. As shown in FIGS. 1 and 2, the portion of the dilation wires 14 that is positioned in the dilation wire lumens 34 in the retracted position may be positioned adjacent the outer surface 40 of the balloon 12 when the dilation wires 14 are extended. The proximal ends 56 of the dilation wires 14 may be connected to a ring 58, or moveable member, at the proximal portion 20 of the shaft 16. The ring 58 is slidable about the shaft 16 in the proximal and distal directions so that the dilation wires 14 may move together when the ring 58 is moved. A proximal stop 60 and a distal stop 62 may also be provided. As shown in FIG. 2, the proximal stop 60 may be formed by a surface 64 of the manifold 22 which extends outward from the shaft diameter 66 on which the ring 58 slides. Thus, as shown in FIG. 1, the ring 58 abuts the proximal stop 60 when the dilation wires 14 are retracted. As shown in FIG. 1, the distal stop 62 may be formed by the proximal ends 68 of the dilation wire lumens 34. Thus, as shown in FIG. 2, the ring 58 abuts the distal stop 62 when the dilation wires 14 are extended. However, other types of stops are also possible.

Figure 4:
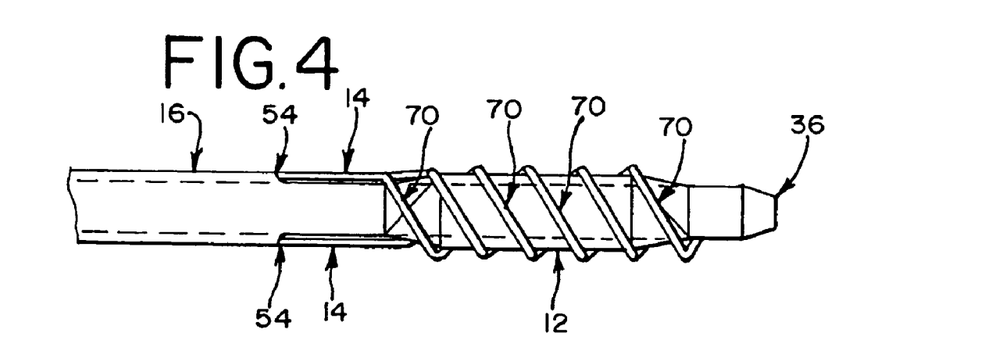
FIG. 4 is a side elevational view of another balloon catheter, showing the balloon deflated and helical dilation wires extended.

As shown in FIG. 4, the dilation wires 14 may be made from a superelastic alloy, such as nitinol. The dilation wires 14 may thus be formed to have non-linear shapes 70 in their relaxed state. As shown, the non-linear shapes 70 of the dilation wires 14 may be helixes that wrap around the balloon 12 in the extended position. However, other non-linear shapes are also possible. When the dilation wires 14 are retracted into the dilation wire lumens 34, the dilation wire lumens 34 straighten the non-linear shapes 70 of the dilation wires 14 to permit the dilation wires 14 to retract into the dilation wire lumens 34.

Figure 5:
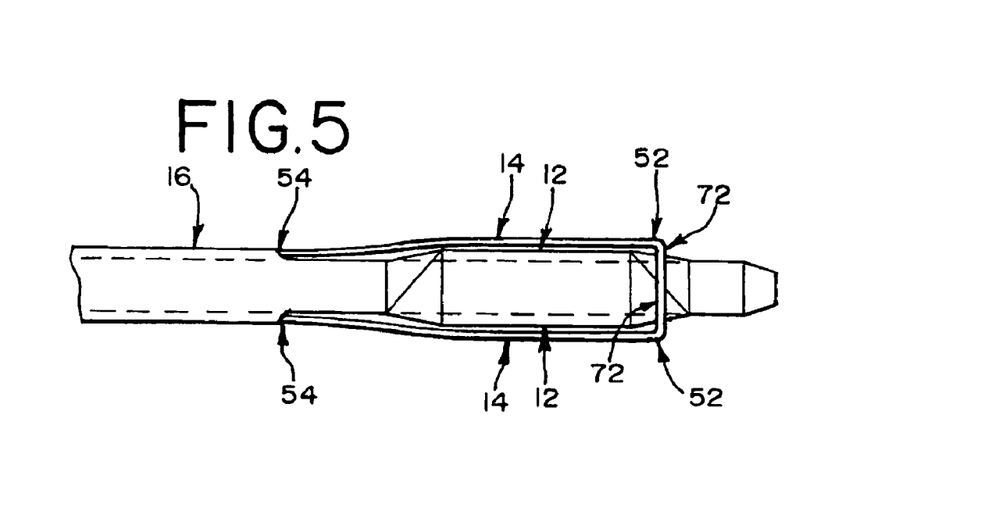
FIG. 5 is a side elevational view of another balloon catheter, showing the balloon deflated and dilation wires extended, where the distal ends of the dilation wires are interconnected by a connecting ring.

As shown in FIG. 5, an annular connector 72 may also be provided. The distal ends 52 of the dilation wires 14 may be attached to the annular connector 72. This may have the advantage of keeping the dilation wires 14 aligned relative to each other in the extended position. Preferably, the annular connector 72 is sized so that it may encircle the balloon 12 when it is deflated to permit the annular connector 72 to move in the proximal and distal directions relative to the deflated balloon 12.

Figure 6:
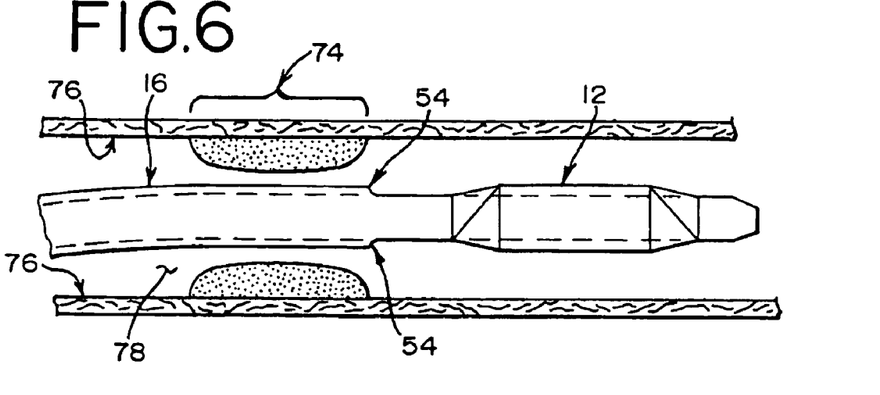
FIG. 6 is a partial cross-sectional view of the balloon catheter of FIGS. 1 and 2 introduced into a stenosed artery, showing the balloon deflated and the dilation wires retracted.

One preferred method for using the balloon catheter 10 is shown in FIGS. 6 through 11. As shown in FIG. 6, the balloon catheter 10 may be threaded to the stenosed region 74 with the dilation wires 14 retracted. It may be preferable to have the distal ends 52 of the dilation wires 14 fully retracted into the dilation wire lumens 34 during the threading procedure to prevent the distal ends 52 from contacting or catching on the vessel wall 76 or other structures. The shaft 16 may then be positioned so that the dilation wires 14 are adjacent the stenosed region 74 while the dilation wires 14 are in the retracted position. At this stage, the ring 58 preferably abuts the proximal stop 60 as shown in FIG. 1.

Figure 7:
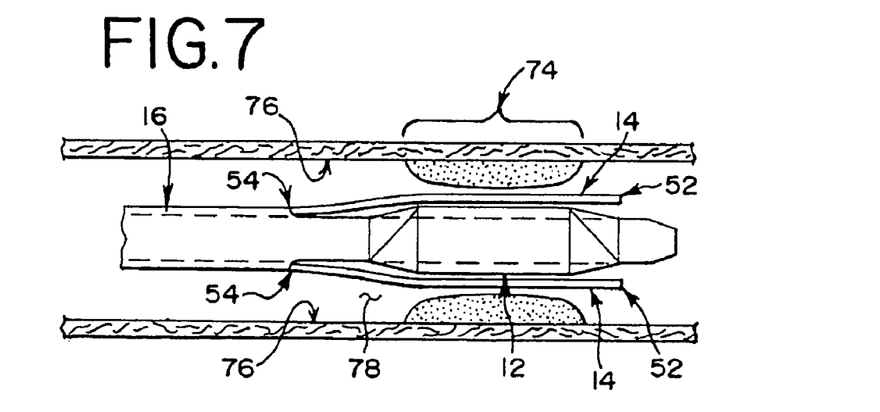
FIG. 7 is a partial cross-sectional view of the balloon catheter of FIGS. 1 and 2 introduced into a stenosed artery, showing the balloon deflated and the dilation wires extended.

As shown in FIG. 7, the dilation wires 14 may be extended by pulling the shaft 16 in the proximal direction while holding the ring 58 to prevent the dilation wires 14 from moving. Thus, the dilation wires 14 do not generally move relative to the stenosed region 74 during the extension. This may be a preferable procedure compared to pushing the dilation wires 14 in the distal direction during extension in order to prevent the distal ends 52 of the dilation wires 14 from catching on the stenosed region 74 or the vessel wall 76. Preferably, the ring 58 abuts the distal stop 62 as shown in FIG. 2 in the extended position to provide the physician with a clear indication of when the dilation wires 14 have reached the extended position.

Figure 8:
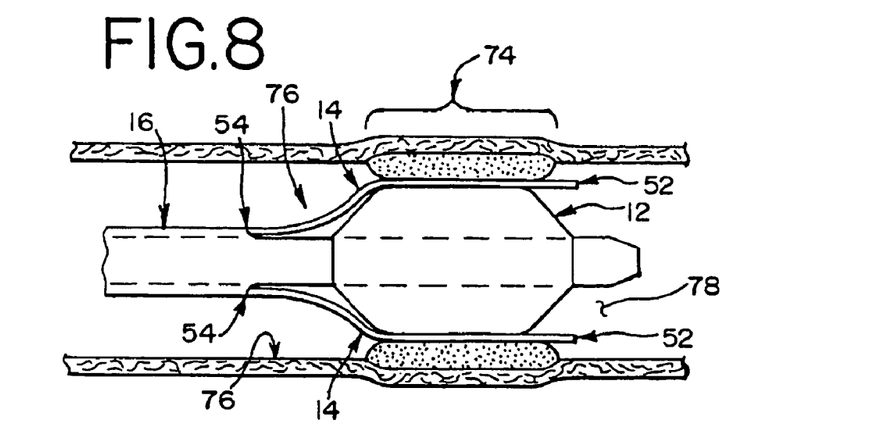
FIG. 8 is a partial cross-sectional view of the balloon catheter of FIGS. 1 and 2 introduced into a stenosed artery, showing the balloon inflated and the dilation wires extended.
Figure 9:
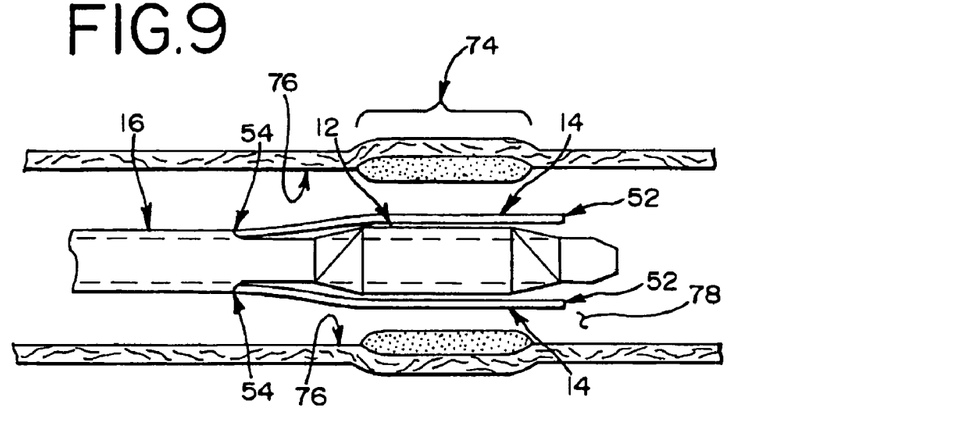
FIG. 9 is a partial cross-sectional view of the balloon catheter of FIGS. 1 and 2 introduced into a stenosed artery, showing the balloon deflated and the dilation wires extended after the stenosed region has been dilated.

As shown in FIG. 8, the balloon 12 may then be inflated to dilate the lumen 78 of the vessel. As a result, the dilation wires 14 are squeezed between the outer surface 40 of the balloon 12 and the stenosed region 74. This is particularly helpful for hardened or calcified stenosed regions since the dilation wires 14 may tend to crack or breakup the hardened stenosis. As shown in FIG. 9, the balloon 12 may then be deflated after the lumen 78 has been dilated with the dilation wires 14.

Figure 10:
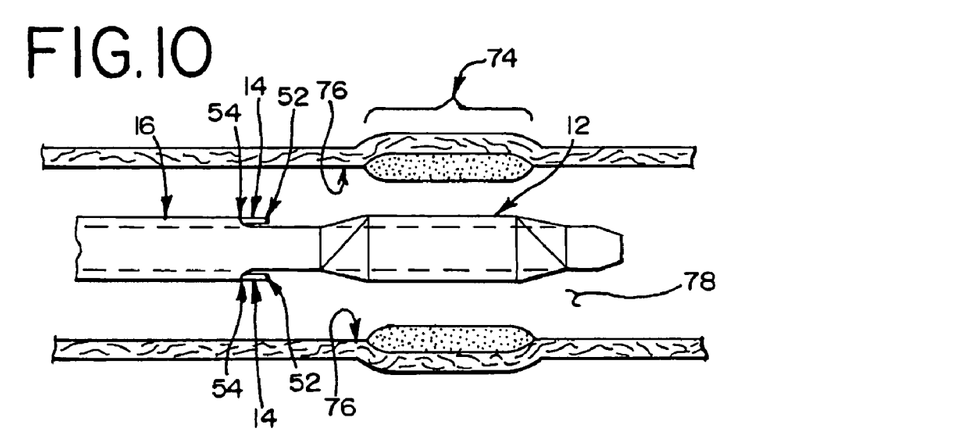
FIG. 10 is a partial cross-sectional view of the balloon catheter of FIGS. 1 and 2 introduced into a stenosed artery, showing the balloon deflated and the dilation wires retracted after the stenosed region has been dilated.

As shown in FIG. 10, the dilation wires 14 may be retracted after the first dilation. Preferably, this is accomplished by pulling on the ring 58 in the proximal direction while preventing the shaft 16 from moving. Thus, the balloon 12 does not generally move relative to the stenosed region 74. Once the ring 58 abuts the proximal stop 60 as shown in FIG. 1, the physician is provided with a clear indication that the dilation wires 14 have reached the retracted position.

Figure 11:
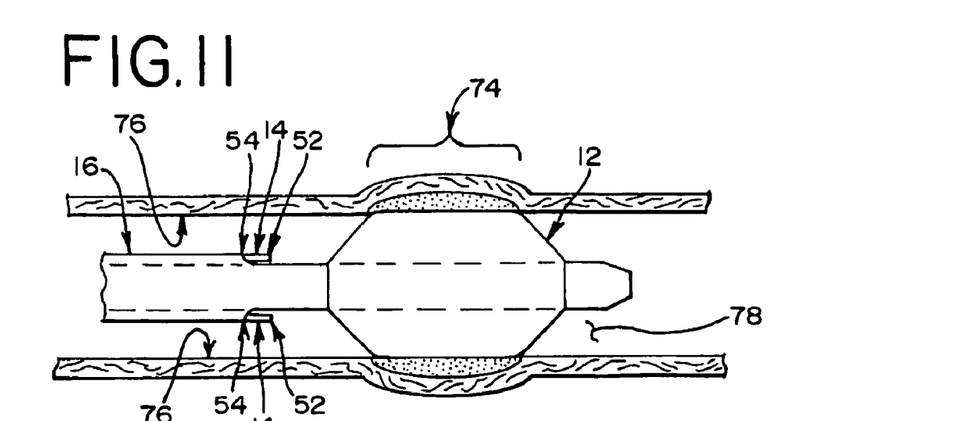
FIG. 11 is a partial cross-sectional view of the balloon catheter of FIGS. 1 and 2 introduced into a stenosed artery, showing the balloon inflated and the dilation wires retracted.

As shown in FIG. 11, the physician may then dilate the lumen 78 of the vessel a second time by re-inflating the balloon 12. A second inflation without the dilation wires 14 may be desirable to fully treat the stenosis and ensure that stenosed region 74 has been fully dilated. After the lumen 78 is re-dilated, the balloon 12 may be deflated and the balloon catheter 10 may be withdrawn. Thus, one advantage of the retractable dilation wires 14 is that the physician may dilate the lumen 78 without having to completely withdraw the balloon catheter 10 and re-introduce a conventional angioplasty balloon catheter. Thus, a single balloon catheter may be used to treat a stenosed region by dilating the lumen with dilation wires and without dilation wires depending on the particular needs of the region being treated.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A balloon catheter for dilation of a lumen, comprising:
a shaft extending between a proximal portion and a distal portion, said distal portion adapted to be introduced into a body lumen, and said proximal portion adapted to remain outside of said body lumen to manipulate said distal portion;
a balloon mounted on said distal portion of said shaft, said shaft having an inflation lumen extending therethrough in fluid communication with an interior region of said balloon, said balloon thereby being expandable between a deflated state and an inflated state, wherein at least a length of an outer surface of said balloon comprises a working diameter adapted to dilate said body lumen, said length extending between a balloon proximal end and a balloon distal end;

a guidewire lumen extending through at least a portion of said shaft and an entirety of said balloon;

at least two dilation wires extending within said shaft from said distal portion of said shaft to said proximal portion of said shaft, wherein each of said dilation wires is positionable between a retracted position and an extended position, wherein, in said retracted position, substantially an entirety of each of said dilation wires is disposed externally of said guide wire lumen within said shaft, and wherein, in said extended position, at least a proximal portion of each of said dilation wires is disposed externally of said guide wire lumen within said shaft, wherein a distal end of each of said dilation wires is disposed proximal from said balloon proximal end in said retracted position, and said distal end of each of said dilation wires is disposed distal from said balloon proximal end in said extended position, said dilation wires thereby being disposed adjacent at least a portion of said working diameter of said balloon in said extended positions, wherein when said balloon is expanded against a stenosis, said dilation wires contact and crack or break-up said stenosis; and a moveable member disposed on said shaft and connected to a proximal end of each of said dilation wires, whereby movement of said moveable member relative to said shaft causes said dilation wires to move together between said retracted position and said extended position.

2. The balloon catheter according to claim 1, further comprising a proximal stop and a distal stop, said moveable member being disposed between said proximal stop and said distal stop, wherein said moveable member abuts said proximal stop when said dilation wires are in said retracted position and said moveable member abuts said distal stop when said dilation wires are in said extended position.

3. The balloon catheter according to claim 1, further comprising at least two dilation wire lumens extending longitudinally through said shaft, one of said dilation wires being disposed within each of said dilation wire lumens, wherein each of said dilation wire lumens has a distal opening and said dilation wires are extendable and retractable through said distal openings, a wire length of each of said dilation wires thereby being disposed within each of said dilation wire lumens in said retracted position and said wire length being disposed adjacent said working diameter of said balloon in said extended position.

4. The balloon catheter according to claim 3, wherein said dilation wires are made of superelastic alloy, each of said dilation wires being formed to have a non-linear shape in a relaxed state, whereby said non-linear shapes are straightened by said dilation wire lumens in said retracted position and said non-linear shapes are released in said extended position, said non-linear shapes of said dilation wires thereby being disposed adjacent said working diameter of said balloon in said extended positions.

5. The balloon catheter according to claim 4, further comprising an annular connector attached to said distal ends of said dilation wires.

6. The balloon catheter according to claim 1, further comprising an annular connector attached to said distal ends of said dilation wires.

7. The balloon catheter according to claim 1, further comprising at least two dilation wire lumens extending longitudinally through said shaft, each of said dilation wire lumens having a distal opening, one of said dilation wires being disposed within each of said dilation wire lumens, said dilation wires being extendable and retractable through said distal openings, wherein a wire length of each of said dilation wires is disposed within each of said dilation wire lumens in said retracted position and said wire length is disposed adjacent said working diameter of said balloon in said extended position.

8. The balloon catheter according to claim 7, further comprising a proximal stop and a distal stop, said moveable member being disposed between said proximal stop and said distal stop, wherein said moveable member abuts said proximal stop when said dilation wires are in said retracted position and said moveable member abuts said distal stop when said dilation wires are in said extended position, and wherein said dilation wires are made of superelastic alloy, each of said dilation wires being formed to have a non-linear shape in a relaxed state, whereby said non-linear shapes are straightened by said dilation wire lumens in said retracted position and said non-linear shapes are released in said extended position, said non-linear shapes of said dilation wires thereby being disposed adjacent said working diameter of said balloon in said extended positions.

9. A balloon catheter for dilation of a lumen, comprising:

a shaft extending between a proximal portion and a distal portion, said distal portion adapted to be introduced into a body lumen, and said proximal portion adapted to remain outside of said body lumen to manipulate said distal portion;

a balloon mounted on said distal portion of said shaft, said shaft having an inflation lumen extending therethrough in fluid communication with an interior region of said balloon, said balloon thereby being expandable between a deflated state and an inflated state, wherein at least a length of an outer surface of said balloon comprises a working diameter adapted to dilate said body lumen, said length extending between a balloon proximal end and a balloon distal end;

a guidewire lumen extending through at least a portion of said shaft and an entirety of said balloon;

at least two dilation wires extending within at least said distal portion of said shaft, each of said dilation wires comprising a distal end, said distal ends characterized by not being connected to each other, wherein each of said dilation wires is positionable between a retracted position and an extended position, wherein, in said retracted position, substantially an entirety of each of said dilation wires is disposed externally of said guide wire lumen within said shaft, and wherein, in said extended position, at least a proximal portion of each of said dilation wires is disposed externally of said guide wire lumen within said shaft, wherein said distal end of each of said dilation wires is disposed proximal from said balloon proximal end in said retracted position, and said distal end of each of said dilation wires is disposed distal from said balloon proximal end in said extended position, said dilation wires thereby being disposed adjacent at least a portion of said working diameter of said balloon in said extended positions, wherein when said balloon is expanded against a stenosis, said dilation wires contact and crack or break-up said stenosis; and a moveable member disposed on said shaft and connected to a proximal end of each of said dilation wires, whereby movement of said moveable member relative to said shaft causes said dilation wires to move together between said retracted position and said extended position.

10. The balloon catheter according to claim 9, further comprising a proximal stop and a distal stop, said moveable member being disposed between said proximal stop and said distal stop, wherein said moveable member abuts said proximal stop when said dilation wires are in said retracted position and said moveable member abuts said distal stop when said dilation wires are in said extended position.

11. The balloon catheter according to claim 9, further comprising at least two dilation wire lumens extending longitudinally through said shaft, one of said dilation wires being disposed within each of said dilation wire lumens, wherein each of said dilation wire lumens has a distal opening and said dilation wires are extendable and retractable through said distal openings, a wire length of each of said dilation wires thereby being disposed within each of said dilation wire lumens in said retracted position and said wire length being disposed adjacent said working diameter of said balloon in said extended position.

12. The balloon catheter according to claim 11, wherein said dilation wires are made of superelastic alloy, each of said dilation wires being formed to have a non-linear shape in a relaxed state, whereby said non-linear shapes are straightened by said dilation wire lumens in said retracted position and said non-linear shapes are released in said extended position, said non-linear shapes of said dilation wires thereby being disposed adjacent said working diameter of said balloon in said extended positions.

13. The balloon catheter according to claim 12, further comprising a proximal stop and a distal stop, said moveable member being disposed between said proximal stop and said distal stop, wherein said moveable member abuts said proximal stop when said dilation wires are in said retracted position and said moveable member abuts said distal stop when said dilation wires are in said extended position.

* * * * *